United States Patent [19]

Feuer et al.

[11] 3,935,219

[45] Jan. 27, 1976

[54] ANTIMICROBIAL DIHALONITROMETHYLISOXAZOLES

[75] Inventors: Henry Feuer, West Lafayette, Ind.; John Pennington Lawrence, Stow, Ohio

[73] Assignee: Purdue Research Laboratory, Lafayette, Ind.

[22] Filed: Oct. 25, 1973

[21] Appl. No.: 409,558

[52] U.S. Cl...... 260/307 H; 260/302 R; 260/302 A; 260/302 D; 260/304; 260/306.7; 260/307 R; 260/307 D; 260/307 F; 260/307 G; 260/999
[51] Int. Cl.² ...................................... C07D 261/08
[58] Field of Search ............................... 260/307 H

[56] References Cited
UNITED STATES PATENTS
3,410,860   11/1968   Haber et al. ....................... 260/296

Primary Examiner—Raymond V. Rush
Attorney, Agent, or Firm—Joseph A. Jones; Everet F. Smith

[57] ABSTRACT

Dihalonitromethylisoxazoles have been prepared from the corresponding nitronate salts. The compounds are useful as broad spectrum antibacterials, antifungals, antiprotozoals and aquatic biocides.

4 Claims, No Drawings

ANTIMICROBIAL DIHALONITROMETHYLISOXAZOLES

BACKGROUND OF THE INVENTION

The invention herein described was made in the course of or under a contract with the Office of Naval Research, Department of the Navy.

This invention concerns novel dihalonitromethyl heterocyclic ring compounds which are useful in the control of a variety of harmful microorganisms.

The nitration of active methylene compounds containing an activating group such as an ester, ketone or cyano group has been previously described. See Feuer et al., *J. Am. Chem. Soc.*, 78, 4364 (1956), Ibid., 81, 5826 (1959), *J. Org. Chem.*, 29, 939 (1964), Ibid., 31, 3152 (1966), Ibid., 34, 991 (1969); and Klager, Ibid., 20, 646 (1955).

In addition, p-anisylnitromethane and its ring nitro derivatives have been prepared by Zalukajevs et al., *Latvijas P.S.R. Zinatnu Akad. Vestis*, 109 (1956). The same auther also prepared α-naphthylnitromethane, *J. Gen. Chem. U.S.S.R.*, 26, 657 (1956).

Primary or secondary nitro compounds form nitronate salts which react with bromine to form bromonitro compounds. In the case of α-nitrocyclic ketones, cleavage can occur upon bromination. See Feuer et al., *J. Org. Chem.*, 29, 939 (1964), Ibid., 33, 3622 (1968), Ibid., 34, 991 (1969). The preparation of halo derivatives of various nitromethyl heterocycles was recently disclosed by Feuer et al., *J. Org. Chem.*, 37, 3662 (1972). Zalukajevs et al. prepared the halo derivatives of 2-nitromethylquinoline, *Zhur. Obshchei Khim.*, 28, 483 (1958).

There is no suggestion in any of the above-described publications that any of the compounds possess antimicrobial activity.

Belgian Patent No. 702,570 discloses 1-aryl-2-nitrohaloethanes useful in the control of bacteria, fungi and algae in water and aqueous compositions. Gum et al., U.S. Pats. Nos. 3,703,515 and 3,754,042, disclose dihalonitromethylsutstituted quinoxalines and cycloalkanes, respectively, which are said to have antimicrobial activity.

SUMMARY

This invention provides to the art a class of novel dihalonitromethyl heterocyclic ring compounds which possess strong activity against bacteria, fungi, and protozoa. Such compounds are those having the formula $$R - CX_2NO_2$$

wherein X represents chloro or bromo;
R represents

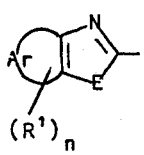, 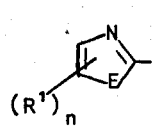, 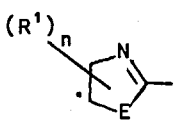,

E represents oxygen or sulfur;
Ar combined with the two carbon atoms to which it is attached forms phenyl or naphthyl;
each of the $R^1$ groups independently represents $C_1-C_3$ alkyl or phenyl;
$n$ represents 0–2 when $R^1$ represents $C_1-C_3$ alkyl;
$n$ represents 0 or 1 when $R^1$ represents phenyl;
$R^2$ represents hydrogen, $C_1-C_3$ alkyl, or phenyl;
$R^3$ represents hydrogen or $C_1-C_3$ alkyl;
$R^4$ represents $C_1-C_3$ alkyl.

DESCRIPTION OF THE PREFERRED EMBODIMENT

The compounds of this invention are characterized by a dihalonitromethyl group attached to a heterocyclic ring, which may be substituted with lower alkyl or phenyl groups.

The term $C_1-C_3$ alkyl is used in the formula above to refer to alkyl groups such as methyl, ethyl, n-propyl and isopropyl.

The term Ar is used in the structures above to indicate that the scope of this invention includes fused-ring compounds wherein a thiazole or oxazole ring is fused to a phenyl or naphthyl ring to form compounds wherein the dihalonitromethyl group is 2-substituted on rings such as benzoxazole and naphthothiazole.

While the generic formula above describes the compounds unambiguously, the following compounds are named to assure that those skilled in the art understand the invention.

2-dichloronitromethyl-1,3,4-oxadiazole
2-dibromonitromethyl-5-isopropyl-1,3,4-oxadiazole
2-dibromonitromethyl-5-phenyl-1,3,4-oxadiazole
2-dichloronitromethyl-1,3,4-thiadiazole
2-dichloronitromethyl-5-phenyl-1,3,4-thiadiazole
2-dichloronitromethyl-5-methyl-1,3,4-thiadiazole
2-dibromonitromethyl-2-oxazoline
2-dibromonitromethyl-4,5-diethyl-2-oxazoline
2-dibromonitromethyl-5-isopropyl-2-oxazoline
2-dichloronitromethyl-4-phenyl-2-oxazoline
2-dichloronitromethyl-5-ethyl-2-thiazoline
2-dichloronitromethyl-2-thiazoline     2-dibromonitromethyl-4,5-dimethyl-2-thiazoline
2-dichloronitromethyl-4-phenyl-2-thiazoline
2-dibromonitromethylthiazole
2-dibromonitromethyl-4,5-dimethylthiazole

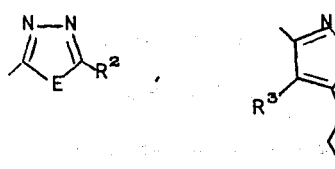, or 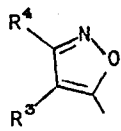 ;

2-dichloronitromethyl-4-ethylthiazole
2-dibromonitromethyl-5-phenylthiazole
2-dichloronitromethyloxazole
2-dichloronitromethyl-4-phenyloxazole
2-dichloronitromethyl-4-propyloxazole
2-dibromonitromethyl-4,5-diethyloxazole
3-dichloronitromethyl-5-phenylisoxazole
5-dichloronitromethyl-3,4-dimethylisoxazole
5-dibromonitromethyl-3-isopropylisoxazole
2-dibromonitromethylbenzothiazole
2-dibromonitromethyl-5-ethylbenzothiazole
2-dichloronitromethyl-4,6-dimethylbenzothiazole
2-dibromonitromethyl-6-phenylbenzothiazole
2-dibromonitromethyl-4-phenylbenzoxazole
2-dichloronitromethyl-7-ethylbenzoxazole
2-dibromonitromethylbenzoxazole
2-dibromonitromethyl-5,7-diethylbenzoxazole
2-dibromonitromethylnaphtho[1,2-d]thiazole
2-dichloronitromethyl-5-phenylnaphtho[2,1-d]thiazole
2-dichloronitromethyl-4,6-diethylnaphtho[2,1-d]thiazole
2-dichloronitromethyl-8-ethylnaphtho[1,2-d]thiazole
2-dichloronitromethyl18-methylnaphtho[1,2-d]oxazole
2-dichloronitromethyl-6,9-dipropylnaphtho[2,1d]oxazole
2-dichloronitromethylnaphtho[1,2-d]oxazole
2-dibromonitromethyl-5-phenylnaphtho[2,1-d]oxazole A preferred subgenus of this invention comprises compounds wherein the R group contains a ring oxygen atom. The preferred individual compounds of the invention are 3-dibromonitromethyl-5-phenylisoxazole, 2-dibromonitromethylbenzoxazole, 3-dichloronitromethyl-5-phenylisoxazole, 5-dichloronitromethyl-3-methylisoxazole, and 2-dichloronitromethyl-2-oxazoline.

The compounds of this invention are easily prepared in a two-step synthesis from methyl-substituted heterocyclic ring compounds having the desired $R^1$, $R^2$, $R^3$, or $R^4$ substituents. Such compounds are commercially available or can be prepared using known procedures in the chemical literature.

The first step of the synthesis is the formation of a nitronate salt, having the structure
$$R - CH = NO_2^- M^+$$
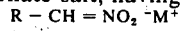
In the formula, R represents the heterocyclic ring described above, and M represents alkali metal, preferably potassium.

Nitronate salts are formed by the procedure described by Feuer et al., J. Am. Chem Soc., 91, 1856 (1969). A methyl heterocycle is treated with an alkali metal amide in liquid ammonia, followed by n-propyl nitrate as the nitrating agent. The reaction is conducted at a temperature from −75° to −30°C. and is generally complete in less than one-half hour. For a discussion of possible variations in the formation of nitronate salts, including solvent effects and the different bases that may be employed, see Feuer et al., J. Am. Chem. Soc., 78, 4364 (1956). One skilled in the art will also recognize that other nitrating agents, such as amyl nitrate, can be used in the formation of nitronate salts.

The nitronate salt is converted to the dihalonitromethyl compounds of the present invention by treatment with a halogenating reagent. The dichloro compounds can be prepared from the nitronate salts by treating with an agent such as potassium hypochlorite at temperatures between −10°C. and 20°C. The corresponding dibromo compounds are best prepared by treatment with bromine in potassium hydroxide solution under similar conditions. The use of a two-fold excess of the aqueous halogenating reagent forms the dihalonitro compound, usually in less than one hour.

The preparative examples below illustrate the methods by which the compounds are made, and are not intended to limit the scope of the invention in any way. The first example shows the synthesis of a typical nitronate salt.

EXAMPLE 1 potassium 3-methyl-5-phenylisoxazolenitronate

Liquid ammonia, 250 ml., was placed in a flask equipped with a mechanical stirrer, thermometer, and Dry Ice condenser. With the temperature kept below −33°C. by external cooling using a Dry ice-acetone bath, a catalytic amount of ferric nitrate monohydrate was added, followed by 5.9 g. of metallic potassium. The mixture was stirred at temperatures below −33°C. until the mixture formed a gray suspension. To the ammonia solution was then added 15.8 g. of 3-methyl-5-phenylisoxazole in 30 ml. of anhydrous ethyl ether, and the mixture was stirred at reflux (approximately −33°C.) for 15 minutes more. the mixture was then cooled to −40°C. to −50°C., and 20.9 g. of n-propyl nitrate was added at such a rate as to control the temperature below −35°C. After stirring for 30 minutes at −33°C., the ammonia was allowed to evaporate and was replaced with 200 ml. of ethyl ether. The solid which formed was filtered, washed with ethyl ether, and dried under vacuum. The product, potassium 3-methyl-5-phenylisoxazolenitronate, was obtained in a sufficiently pure form to use in the following step without further purification. The yield was 20.9 g.

The intermediate nitronate salts are converted to the new dihalonitromethyl compounds by processes typified by the following example.

EXAMPLE 2

3-dibromonitromethyl-5-phenylisoxazole

A 5.9 g. portion of the nitronate salt made in Example 1 was dissolved in 45 ml. of water, and the solution was filtered. The solution was then added to a solution of 15.1 g. of KOH and 15.1 g. of bromine in 60 ml. of water at 0°–5°C. The reaction mixture was stirred for 1 hour at about 5°–10°C. during which time a precipitate formed. The solids were collected by filtration, washed with water and dried. The product was recrystallized from hexane, and identified by nuclear magnetic resonance analysis. The yield was 0.50 g. of 3-dibromonitromethyl-5-phenylisoxazole (I), m.p. 72°–74°C.

The following exemplary compounds were made by the processes of Examples 1 and 2 with small modifications which can readily be supplied by one skilled in the art.

2-dichloronitromethylnaphtho[2,1-d]thiazole (II), m.p. 114°–116°C.
2-dibromonitromethylbenzoxazole (III), m.p. 76°–80°C.
2-dibromonitromethylnaphtho[1,2-d]thiazole (IV), m.p. 116°–117°C.
2-dichloronitromethyl-5-methyl-1,3,4-thiadiazole (V), oil
2-dichloronitromethyl-4-methylthiazole (VI), oil 4-dibromonitromethyl-2-methylthiazole (VII), 95-9-5-98°c.
5-dibromonitromethyl-3-methylisoxazole (VIII), m.p. 59°-62°C.
5-dichloronitromethyl-3-methylisoxazole (IX), oil
3-dichloronitromethyl-5-phenylisoxazole (X), m.p. 65°-67°C.
2-dichloronitromethyl-2-oxazoline (XI), oil
2-dichloronitromethylnaphtho[1,2-d]thiazole (XII), m.p. 108°-112°C.
2-dichloronitromethylbenzothiazole (XIII), m.p. 38°38°43°C.
2-dichloronitromethylbenzoxazole (XIV), m.p. 41°-45°C.
2-dibromonitromethylbenzothiazole (XV), m.p. 71°-73°C.
2-dibromonitromethyl-5-methyl-1,3,4-thiadiazole (XVI), m.p. 76°-72°C.
2-dibromonitromethylnaphtho[2,1-d]thiazole (XVII), m.p. 129°-130°C.
2-dichloronitromethyl-2-thiazoline (XVIII), m.p. 58°-62°C.
2-dibromonitromethyl-2-oxazoline (XIX), m.p. 60°-62°C.

The compounds of the present invention are biocides in a broad sense. As the examples below indicate, the compounds kill or control microorganisms such as bacteria, fungi, protozoa, and algae, as well as some aquatic weeds. Those skilled in the art will appreciate that the biocidal properties of the compounds make them useful in many ways.

For example, the compounds can be added to bodies of water such as cooling towers and ponds, lagoons, lakes and the like for the control of aquatic weeds, algae, and slime-forming microorganisms. The control is brought about by adding an effective, economical amount such as from about 0.1 to about 100 ppm. of the compound to the water to be protected from aquatic organisms. It is often convenient to formulate the compound in an easily water-dispersible mixture before addition. Such formulations are known to the art, and comprise a finely divided powder, or a solution or suspension of the compound in a liquid such as water or an organic solvent, to which surfactants such as ethylene oxide adducts of nonylphenol and alkylbenzenesulfonates are often added to increase the dispersibility of the mixture.

The compounds can also be added to such compositions as adhesives, inks, plasticizers, latices, polymers, resins, fuels, lubricants, soaps and detergents, cutting oils, and paints to prevent the growth of mold and the degradation of the products which results from attack by microorganisms.

The compounds can also be coated on or distributed through products such as textiles, paper and other cellulose products and may be impregnated into wood, wall paneling and plaster to protect such products from mold and decay caused by microbial infestation. The compounds are especially useful for the preservation of such products as cosmetic formulations.

The compounds are valuable disinfectants and sterilizing agents for surfaces such as floors, walls, hospital equipment, kitchen equipment and the like.

The compounds of this invention can be used to control microorganisms, especially fungi, growing on the skin and outer tissues of animals. The examples below show, for example, that the compounds are especially effective in the control of *Candida tropicalis* and *Trichomonas vaginalis*, both of which are important causes of vaginal infections. The compounds are used for the control of such infections by formulating them into ointments, creams and the like according to the usual pharmaceutical methods and applying them topically to the site of the infection.

The outstanding efficacy of the compounds against representative microorganisms is illustrated by the examples below.

EXAMPLE 3 in vitro agar dilution test

Bacteria and fungi in an agar medium were stamped on a plate to which one drop of a 100 $\mu$g./ml. or a 10 $\mu$g./ml. solution of the compound was surface applied. The agar plates were then incubated at 35°C. for 12 hours, at which time the antibacterial activities were evaluated. The fungi were incubated at 25°C. for an additional 60 hours before evaluation. The procedure was essentially that recommended in *Acta Pathol. Microbiol. Scand. B.,* Suppl. 217, 11 (1971). A rating of 100 indicates that the compound prevented growth of the microbe at 100 $\mu$g./ml. and 10 indicates prevention at the 10 $\mu$g./ml. level. NT indicates the compound was not tested for activity against an organism, while a blank space indicates the compound was not active at the highest level tested (100 $\mu$g./ml.).

| Compound | Staphylococcus aureus | Streptococcus faecalis | Proteus | Salmonella typhosa | Klebsiella-aerobacter sp. KA14 | Klebsiella-aerobacter sp. KA17 | Escherichia coli | Pseudomonas aeruginosa | C-476 |
|---|---|---|---|---|---|---|---|---|---|
| I | 10 | 100 | 100 | 100 | 10 | 10 | 10 | 100 | 100 |
| II | 10 | 10 | 10 | | | | | | |
| III | 10 | 10 | 100 | 10 | 10 | 10 | 10 | 10 | 10 |
| VII | | | | | | | | | |
| X | 10 | 10 | 10 | 10 | 10 | 10 | 10 | 10 | 100 |
| XII | 100 | 100 | | | | | | | |
| XIII | 100 | 100 | 100 | 100 | | 100 | | | 100 |
| XIV | 10 | 100 | 100 | 100 | 100 | 100 | 10 | 100 | 100 |
| XVIII | 100 | 100 | 100 | 100 | 100 | 100 | 100 | | 100 |

| Compound | Salmonella typhimurium | Pseudomonas solanacearum | Erwinia amylovora | Xanthomonas phaseoli | Candida tropicalis | Trichophyton mentagrophytes | Botrytis cinerea | Ceratocystis ulmi | Fusarium oxysporum F. lycopersici | Verticillium albo-atrum |
|---|---|---|---|---|---|---|---|---|---|---|
| I | 10 | 10 | 100 | 10 | 100 | 10 | 10 | 10 | 100 | 10 |
| II | | | 100 | | | | 100 | 100 | | 100 |
| III | 10 | 10 | 10 | 10 | | 10 | 10 | 100 | 100 | 10 |
| VII | | | | | | | 100 | | | |
| X | 10 | 10 | 100 | 10 | 10 | 10 | 10 | 10 | 10 | 10 |

-continued

| Compound | Staphylococcus aureus | Streptococcus faecalis | Proteus | Salmonella typhosa | Klebsiella-aerobacter sp. KA14 | Klebsiella-aerobacter sp. KA17 | Escherichia coli | Pseudomonas aeruginosa | C-476 |
|---|---|---|---|---|---|---|---|---|---|
| XII | | | | | | | | | |
| XIII | 100 | | 100 | 100 | | 100 | 100 | 100 | 100 |
| XIV | 100 | 100 | 100 | 100 | | 10 | 10 | | |
| XVIII | 100 | 100 | 100 | 100 | 100 | 10 | 100 | 100 | 100 |

| Compound | Staphyloccus aureus 3055 | Staphyloccus aureus 3074 | Streptoccus faecalis X66 | Proteus Morganii Pris | Salmonella typhosa SA12 | Klebsiella pneumoniae KL14 | Enterobacter Aerogenes EB17 |
|---|---|---|---|---|---|---|---|
| IV | 100 | 100 | 100 | 100 | 100 | 100 | 100 |
| V | | | | | | 100 | |
| VI | 100 | 100 | 100 | | 100 | | |
| VIII | 100 | 100 | 100 | 100 | 100 | 100 | 100 |
| IX | 100 | 100 | 100 | 100 | 100 | 100 | 100 |
| XI | 10 | 10 | 100 | 10 | 10 | 100 | 100 |
| XV | 100 | 100 | 100 | 100 | 100 | 100 | 100 |
| XVI | 100 | 100 | 100 | 100 | 100 | 100 | 100 |
| XVII | 100 | 100 | 100 | 100 | 100 | 100 | 100 |
| XIX | 100 | 100 | 100 | 100 | 100 | 100 | 100 |

| Compound | Serratia marcescens SE3 | Escherichia coli EC14 | Citrobacter freundii CF17 | Pseudomonas aeruginosa X239 | Bordetella bronchiseptica 16 | Salmonella typhimurium |
|---|---|---|---|---|---|---|
| IV | 100 | 100 | 100 | 100 | 100 | 100 |
| V | | | | | 100 | |
| VI | | | | | 100 | |
| VIII | 100 | 100 | 100 | 100 | 100 | 100 |
| IX | 100 | 100 | 100 | | 100 | 100 |
| XI | 100 | 10 | 100 | 100 | 10 | 10 |
| XV | 100 | 100 | 100 | 100 | 100 | 100 |
| XVI | 100 | 100 | 100 | 100 | 100 | 100 |
| XVII | 100 | 100 | 100 | 100 | 100 | 100 |
| XIX | 100 | 100 | 100 | 100 | 100 | 100 |

| Compound | Psuedomonas solanacearum X185 | Erwinia amylorora | Candida tropicalis A17 | Trichophyton mentagrophyles 27 | Aspergillis flavis E | Ceratocystis ulmi |
|---|---|---|---|---|---|---|
| IV | 100 | 100 | 100 | 100 | 100 | 100 |
| V | | | 100 | | | 100 |
| VI | | 100 | 100 | 10 | 10 | 10 |
| VIII | 100 | 100 | 100 | 100 | 100 | 100 |
| IX | 100 | 100 | 100 | 10 | 10 | 10 |
| XI | 100 | 10 | 10 | 100 | 100 | 10 |
| XV | 100 | 100 | 100 | 100 | 100 | 100 |
| XVI | | 100 | 100 | 100 | 100 | 100 |
| XVII | | 100 | 100 | 100 | 100 | 100 |
| XIX | 100 | 100 | 100 | 100 | 100 | 100 |

The example below reports representative results of testing the compounds in a slightly different in vitro test against a different group of microorganisms.

EXAMPLE 4 in vitro tube dilution test

The organisms against which the compounds were to be tested were grown in nutrient broth in test tubes under sterile conditions. One hundred μg./ml. of the compound to be tested was added to a tube of broth, and the treated broth was serially diluted with untreated broth in which the culture had been inoculated. The tubes were observed, and the results for each compound were recorded as the lowest concentration, in micrograms per milliliter, in which the compound prevented the growth of the microorganism.

| Compound | Staphylococcus sp. 1130 | Streptococcus sp. 80 | Vibrio coli | Mycoplasma gallisepticum | Escherichia coli | Salmonella dublin | Pseudomonas sp. |
|---|---|---|---|---|---|---|---|
| I | 50 | 50 | 50 | 25 | >50 | >50 | >50 |
| III | 50 | 50 | 25 | 25 | >50 | >50 | 50 |
| IV | >50 | >50 | >50 | 50 | >50 | >50 | >50 |
| V | >50 | 50 | 50 | 25 | >50 | >50 | >50 |
| VI | 12.5 | 12.5 | 25 | 6.25 | 50 | 25 | >50 |
| VII | >50 | 50 | 50 | >50 | >50 | >50 | >50 |
| VIII | >50 | >50 | >50 | 50 | >50 | >50 | >50 |
| IX | 25 | 25 | <.78 | 25 | 50 | 50 | >50 |
| X | 12.5 | 6.25 | 25 | 12.5 | 25 | 25 | 50 |
| XI | 12.5 | 25 | 6.25 | 6.25 | 25 | 25 | >50 |
| XII | 25 | 12.5 | 3.12 | 25 | >50 | >50 | >50 |
| XIII | 50 | 25 | 25 | 12.5 | 50 | 50 | 50 |
| XIV | 25 | 25 | 12.5 | 50 | 50 | 50 | 50 |
| XV | >50 | >50 | >50 | >50 | >50 | >50 | >50 |
| XVI | >50 | >50 | 50 | 50 | >50 | >50 | >50 |
| XVII | >50 | >50 | 50 | 50 | >50 | >50 | >50 |
| XVIII | 12.5 | 6.25 | 6.25 | 6.25 | >50 | >50 | >50 |
| XIX | >50 | >50 | 50 | 25 | >50 | >50 | 50 |

| Compound | Pasteurella multocida | P. multocida turkey isolate | Bordetella | Mycoplasma syroviae | M. hyorhinis | M. granularum |
|---|---|---|---|---|---|---|
| I | 25 | 25 | 50 | 50 | 50 | 25 |
| III | 50 | 50 | 50 | 25 | 50 | >50 |
| IV | 50 | >50 | 50 | 25 | 25 | 50 |
| V | 50 | 50 | 50 | 25 | >50 | 50 |
| VI | 12.5 | 6.25 | 50 | 12.5 | 25 | 12.5 |
| VII | >50 | 50 | >50 | 50 | 50 | 50 |
| VIII | >50 | >50 | >50 | 50 | 50 | >50 |
| IX | 12.5 | 3.12 | 50 | | 50 | 25 |
| X | 3.12 | 3.12 | 12.5 | 12.5 | 50 | 6.25 |
| XI | 6.25 | 12.5 | 12.5 | 12.5 | 50 | 50 |
| XII | 12.5 | 25 | 25 | 12.5 | 25 | 12.5 |
| XIII | 25 | 25 | 50 | 25 | 50 | 25 |
| XIV | 12.5 | 12.5 | 25 | 12.5 | 50 | 25 |
| XV | >50 | >50 | >50 | >50 | >50 | >50 |
| XVI | 50 | 50 | >50 | 50 | 50 | >50 |
| XVII | 50 | >50 | >50 | 50 | 50 | >50 |
| XVIII | 3.12 | 6.25 | 12.5 | 12.5 | 25 | 6.25 |
| XIX | >50 | >50 | >50 | 50 | 50 | 50 |

A generally similar test was performed to evaluate the compounds against additional species of fungi.

EXAMPLE 5 in vitro antifungal test

| Compound No. | Trichophyton mentagrophytes | Candida albicans |
|---|---|---|
| VI | 0.2 µg./ml. | 2.0 µg./ml. |
| VIII | >2.0 | 20 |
| XI | 0.2 | 20 |
| XIII | 0.02 | 0.2 |
| XIV | 0.02 | 2.0 |
| XV | 0.002 | 20 |
| XVI | >2.0 | 20 |
| XVIII | 0.2 | 2.0 |
| XIX | 2.0 | 20 |

In a different antifungal test, the compounds to be tested were absorbed on paper discs, and the discs were laid on plates of fungus-infected agar medium. The results were reported as the last amount of compound per disc which produced a measurable inhibition of the fungus.

| Compound No. | Trichophyton mentagrophytes | Candida albicans |
|---|---|---|
| X | 0.625 µg./ml. | 0.078 µg./ml. |

Compounds of this invention were tested in vitro to determine their ability to control protozoa and algae. The examples below report representative results of such tests.

EXAMPLE 6 in vitro protozoa inhibition tests

The tests were run against four representative protozoa, *Tetrahymena pyriformis* (T), *Ochromonas malhamensis* (O), *Euglena gracilis* (E), and *Trichomonas vaginalis* (TV). The protozoa were grown in the laboratory in nutritive media. When a test was to be run, nutritive medium containing the test protozoa was mixed with sterile agar medium, and the mixed medium poured into plates.

Absorbent discs were treated with 0.02 ml. of a solution containing a known concentration of the compound to be tested. The concentrations used are indicated in the table below. The discs were placed on the surfaces of the protozoa-containing agar plates.

The plates were incubated for a time, and were then inspected to determine if the test compounds absorbed on the discs had inhibited the growth of the protozoa. Inhibition, if present, was measured as the diameter in millimeters of the zones of inhibition surrounding the discs.

The table below reports the zones of inhibition produced by representative compounds of this invention. The notation TR indicates that the compound gives a trace of inhibition. NT indicates that the compound was not tested against a given organism, and a blank space indicates that the compound was inactive.

| Compound No. | Conc. | T | O | E | TV |
|---|---|---|---|---|---|
| I | 2000 | | 17 | 28 | 11 |
| | 500 | | 12 | 17 | TR |
| | 125 | | TR | 10 | |
| III | 2000 | 46 | 25 | 50 | 15 |
| | 500 | 25 | 15 | 20 | 10 |
| | 125 | 14 | 10 | 11 | |
| IV | 2000 | 25 | 25 | 23 | 11 |
| | 500 | 12 | 14 | 10 | |
| | 125 | TR | | | |
| V | 2000 | 26 | 30 | 38 | |
| | 500 | 16 | 17 | 16 | |
| | 125 | 11 | 11 | 11 | |
| VI | 2000 | 17 | 19 | 22 | |
| | 500 | TR | 12 | 11 | |
| X | 2000 | 16 | 18 | 13 | 36 |
| | 500 | 13 | 12 | 12 | 23 |
| | 125 | TR | TR | TR | 15 |
| XI | 2000 | | | | 14 |
| XII | 2000 | | 10 | 17 | |
| | 500 | | | TR | |
| XIII | 2000 | 17 | 25 | 24 | |
| | 500 | 15 | 18 | 17 | |
| | 125 | 13 | 14 | 15 | |
| XIV | 2000 | 24 | 18 | 20 | 12 |
| | 500 | 18 | 17 | 17 | |
| | 125 | 14 | TR | TR | |
| XV | 2000 | 20 | 24 | 25 | TR |
| | 500 | 12 | 11 | 10 | |
| XVI | 2000 | 16 | 18 | 28 | 11 |
| | 500 | 12 | TR | 12 | TR |
| XVII | 2000 | | 26 | 38 | 14 |
| | 500 | | 12 | 18 | TR |
| | 125 | | TR | | |
| XVIII | 2000 | 20 | 17 | 20 | 10 |

-continued

| Compound No. | Conc. | T | O | E | TV |
|---|---|---|---|---|---|
| | 500 | 13 | 12 | 10 | TR |
| | 125 | 12 | 10 | TR | |
| XIX | 2000 | 25 | 17 | 24 | 15 |
| | 500 | 13 | 14 | 12 | TR |

EXAMPLE 7 in vitro algae inhibition test

The activity of the compounds against a typical alga was determined by conducting a test, substantially identical to the test described above, against *Chlorella vulgaris*. Representative results are reported below.

| Compound No. | Conc. | Chlorella |
|---|---|---|
| I | 2000 | 72 |
| | 500 | 32 |
| | 125 | 10 |
| III | 2000 | 77 |
| | 500 | 40 |
| | 125 | 12 |
| IV | 2000 | 39 |
| | 500 | 19 |
| | 125 | |
| V | 2000 | 26 |
| | 500 | 13 |
| | 125 | |
| VI | 2000 | 10 |
| | 500 | |
| X | 2000 | 16 |
| | 500 | 13 |
| | 125 | 11 |
| XI | 2000 | |
| XII | 2000 | TR |
| | 500 | |
| XIII | 2000 | 21 |
| | 500 | 15 |
| | 125 | TR |
| XIV | 2000 | 30 |
| | 500 | 17 |
| | 125 | TR |
| XV | 2000 | 38 |
| | 500 | 16 |
| XVI | 2000 | 42 |
| | 500 | 13 |
| XVII | 2000 | 58 |
| | 500 | 20 |
| | 125 | |
| XVIII | 2000 | 42 |
| | 500 | 23 |
| | 125 | 10 |
| XIX | 2000 | 18 |
| | 500 | 11 |

The tests reported below show the ability of the compounds of the invention to eradicate microorganisms established in a culture.

EXAMPLE 8 in vitro eradication test

Aqueous dispersions of 3-dibromonitromethyl-5-phenylisoxazole were inoculated to contain known concentrations of the organisms shown below. Viable organism counts, in organisms per milliliter, were made initially and after times of 25°C. incubation shown in the table below. A count of less than 100 organisms per milliliter is regarded as equivalent to complete kill of the organism.

| Days | 0.5% of Compound Pseudomonas aeruginosa | Aspergillus niger |
|---|---|---|
| 0 | $3.4 \times 10^6$ | $6 \times 10^3$ |
| 1 | <100 | <100 |
| 7 | <100 | <100 |
| 28 | <100 | <100 |

| Days | 0.1% of Compound Pseudomonas aeruginosa | Aspergillus niger |
|---|---|---|
| 0 | $6.4 \times 10^6$ | $5 \times 10^3$ |
| 1 | <100 | $4 \times 10^3$ |
| 7 | <100 | <100 |
| 14 | NT | <100 |
| 28 | <100 | <100 |

Similar tests were performed with 3-dichloronitromethyl5-phenylisoxazole.

| Days | 0.5% of Compound Pseudomonas aeruginosa | Aspergillus niger |
|---|---|---|
| 0 | $5.9 \times 10^6$ | $1 \times 10^4$ |
| 1 | $1.9 \times 10^5$ | $2.7 \times 10^3$ |
| 7 | <100 | <100 |
| 14 | <100 | <100 |
| 28 | <100 | <100 |

A similar test, against a broader range of microorganisms, was performed with 3-dibromonitromethyl-5-phenylisoxazole as the test compound. In this test, the fungi were inoculated in Sabouraud dextrose agar, and the bacteria in soybean-casein medium. The test was otherwise similar to the test described immediately above.

| | 0.05% of Compound | | | | | |
|---|---|---|---|---|---|---|
| Days | Staphylococcus aureus | Escherichia coli | Pseudomonas aeruginosa | Candida albicans | Aspergillus niger | Streptococcus faecalis |
| 0 | $4.3 \times 10^6$ | $6.9 \times 10^6$ | $4.5 \times 10^6$ | $3.2 \times 10^6$ | $3.2 \times 10^5$ | $2.5 \times 10^6$ |
| 1 | <100 | <100 | <100 | $3.6 \times 10^5$ | $3.9 \times 10^5$ | <100 |
| 7 | <100 | <100 | <100 | $3.7 \times 10^4$ | $4.4 \times 10^5$ | <100 |
| 14 | NT | NT | NT | <100 | $1.7 \times 10^5$ | NT |
| 21 | NT | NT | NT | <100 | $7.5 \times 10^2$ | NT |
| 28 | <100 | <100 | <100 | <100 | <100 | <100 |

The compounds also kill or control many aquatic weeds. For example, hydrilla, coontail, and duckweed were controlled by adding 10 ppm. of 2-dibromonitromethyl-2-oxazoline to the water in which the weeds were growing. Similar weed control was produced by, for example, 3-dichloronitromethyl-5-phenylisoxazole and 2-dibromonitromethylbenzothiazole.

We claim:
1. A compound of the formula
   $R - CX_2NO_2$
wherein X represents chloro or bromo;
R represents

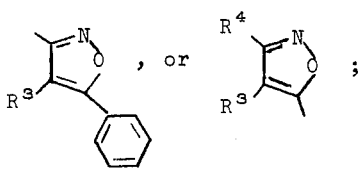
$R^3$ represents hydrogen or $C_1$–$C_3$ alkyl; $R^4$ represents $C_1$–$C_3$ alkyl.
2. The compound of claim 1 which is 3-dibromonitro-methyl-5-phenylisoxazole.
3. The compound of claim 1 which is 3-dichloronitromethyl-5-phenylisoxazole.
4. The compound of claim 1 which is 5-dichloronitromethyl-3methylisoxazole.
* * * * *

UNITED STATES PATENT AND TRADEMARK OFFICE
CERTIFICATE OF CORRECTION

PATENT NO. : 3,935,219
DATED : January 27, 1976
INVENTOR(S) : Henry Feuer et al.

It is certified that error appears in the above-identified patent and that said Letters Patent are hereby corrected as shown below:

Column 2, line 48 should read --2-dichloronitromethyl-2-thiazoline--.

Column 2, line 49 should read --2-dibromonitromethyl-4,5-dimethyl-2-thiazoline--.

Column 3, line 7 should read --3-dichloronitromethyl-5-phenyl-isoxazole--.

Column 3, lines 24 and 25 should read --2-dichloronitromethyl-8-methylnaphtho[1,2-d]oxazole--.

Column 3, lines 26 and 27 should read --2-dichloronitromethyl-6,9-dipropylnaphtho[2,1-d]oxazole--.

Column 5, line 12 should read -- 38°-43°C. --.

Column 5, line 18 should read -- m.p. 67°-72°C. --.

Columns 5 and 6, in the first part of the table, the heading "Streptoccus faecalis" should read --Streptococcus faecalis--.

Columns 7 and 8, in the table continued from the preceeding page, the headings should be deleted and the headings from the second part of the table at Columns 5 and 6 should be inserted.

Column 9, line 45, "last" should be changed to --least--.

Column 14, line 2, "tro-methyl" should be changed to --tromethyl--.

Signed and Sealed this first Day of June 1976

[SEAL]

Attest:

RUTH C. MASON
*Attesting Officer*

C. MARSHALL DANN
*Commissioner of Patents and Trademarks*